(12) United States Patent
Van Gaal et al.

(10) Patent No.: US 9,131,846 B2
(45) Date of Patent: Sep. 15, 2015

(54) OPTICAL SCANNING PROBE ASSEMBLY

(75) Inventors: Franciscus Martinus Antonius Maria Van Gaal, Heeze (NL); Bernardus Hendrikus Wilhelmus Hendriks, Eindhoven (NL); Augustinus Laurentius Braun, Heeze (NL); Cornelius Antonius Hezemans, Nuenen (NL); Waltherus Cornelis Jozef Bierhoff, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 140 days.

(21) Appl. No.: 13/125,392

(22) PCT Filed: Oct. 19, 2009

(86) PCT No.: PCT/IB2009/054593
§ 371 (c)(1),
(2), (4) Date: Apr. 21, 2011

(87) PCT Pub. No.: WO2010/046836
PCT Pub. Date: Apr. 29, 2010

(65) Prior Publication Data
US 2011/0201941 A1  Aug. 18, 2011

(30) Foreign Application Priority Data
Oct. 22, 2008 (EP) .................................. 08167247

(51) Int. Cl.
*A61B 6/00* (2006.01)
*A61B 5/00* (2006.01)
*G02B 23/24* (2006.01)
*G02B 26/10* (2006.01)

(52) U.S. Cl.
CPC ............. *A61B 5/0062* (2013.01); *A61B 5/0084* (2013.01); *G02B 23/2461* (2013.01); *G02B 26/103* (2013.01)

(58) Field of Classification Search
USPC ......... 600/473, 476, 478, 466–467, 433–435; 356/126, 515
See application file for complete search history.

(56) References Cited

U.S. PATENT DOCUMENTS

| | | | |
|---|---|---|---|
| 6,240,231 B1 * | 5/2001 | Ferrera et al. ................. | 385/115 |
| 6,564,087 B1 | 5/2003 | Pitris et al. | |
| 6,687,010 B1 * | 2/2004 | Horii et al. .................... | 356/479 |
| 6,702,802 B1 * | 3/2004 | Hancock et al. .............. | 604/524 |
| 6,967,772 B2 | 11/2005 | Harris | |
| 7,333,700 B2 | 2/2008 | Karasawa | |
| 2003/0088187 A1 * | 5/2003 | Saadat et al. .................. | 600/547 |
| 2004/0254474 A1 * | 12/2004 | Seibel et al. .................. | 600/473 |
| 2005/0168751 A1 * | 8/2005 | Horii et al. .................... | 356/479 |
| 2007/0273930 A1 | 11/2007 | Berier | |
| 2008/0265178 A1 | 10/2008 | Johnston | |

FOREIGN PATENT DOCUMENTS

| | | |
|---|---|---|
| DE | 3904634 A1 | 2/1989 |
| JP | 56153315 | 4/1980 |

(Continued)

*Primary Examiner* — Joel F Brutus

(57) ABSTRACT

An optical scanning probe assembly for microscopic guide optic scanning and inspection of tissues includes an outer housing having a spring element for a scanning motor. The spring element is formed as a hollow tube configured to receive an optical guide, where the hollow tube has a mechanical stiffness larger than the optical guide to be received. The assembly further includes a lens system and a deflector configured to deflect the distal end of the hollow tube in directions transverse to the longitudinal extension of the hollow tube, so as to form an optical scan pattern.

14 Claims, 3 Drawing Sheets

(56) References Cited

FOREIGN PATENT DOCUMENTS

| WO | 9325155 | A1 | 12/1993 |
| WO | 2006004743 | A2 | 1/2006 |
| WO | 2006032106 | A1 | 3/2006 |
| WO | 2006095191 | A1 | 9/2006 |

\* cited by examiner

OPTICAL SCANNING PROBE ASSEMBLY

FIELD OF THE INVENTION

The present invention relates to an optical scanning probe assembly for microscopic fiber optic scanning and inspection of tissues suitable for application in, e.g. in vivo medical inspection.

BACKGROUND OF THE INVENTION

For correct diagnosis of various diseases, e.g. cancer, biopsies are often taken. This can either be performed via a lumen of an endoscope or via needle biopsies. In order to find the correct position where the biopsy has to be taken, various imaging modalities are used such as X-ray, Magnetic Resonance Imaging (MRI) and ultrasound. For example in most of the cases of prostate cancer the biopsy is guided by ultrasound. Although helpful, these methods of guidance are far from optimal. The resolution is limited and, furthermore, these imaging modalities can in most cases not discriminate between benign and malignant tissue.

In order to improve the biopsy procedure direct inspection of the biopsy position, prior biopsy, is required. A way to achieve this direct inspection is by microscopic inspection at the specific position. This requires a miniaturised confocal microscope coupled to an optical fiber probe. However, this system has the drawback that its scanning properties strongly depends on the mechanical properties of the optical guide.

A way to avoid this dependency is described in U.S. Pat. No. 6,967,772 where a scanning fiber system based on an electrically operated tuning fork with an attached fiber is disclosed. The mechanical properties of the scanning system described by the US patent are determined by the tuning fork and not by the fiber. However a disadvantage of this system is that it requires a significant amount of space, due to the dimension of the tuning fork, hampering the downscaling of the system. Furthermore, since the driving frequency of the fiber is in this system the resonance frequency of the tuning fork, non resonant scanning is not possible.

In summary, none of previously disclosed fiber scanning systems solves the problem of how to provide a scanning optical guide system in which the mechanical properties of the scanning system is not determined by the optical guide, without compromising the downscaling of the system.

Hence, an improved scanning system which allows for resonant and non resosonat scanning, which allows for downscaling and in which the mechanical properties are independent from the optical guide used, would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide an optical scanning probe assembly where the mechanical properties of the scanning system are determined by a hollow tube adapted to receive an optical guide and having mechanical stiffness larger than the optical guide to be received. In this probe assembly the optical properties of the system are still determined by the guide, while the mechanical properties depend on the stiffness of the hollow tube without compromising the downscaling of the system.

It is a further object of the present invention to provide an advantageous alternative to the prior art by providing a system which allows for both resonant and non resonant scanning.

This object and several other objects are achieved by providing, in a first aspect, an optical scanning probe assembly that comprises: i) an outer housing comprising a spring element for a scanning motor formed as a hollow tube adapted to receive an optical guide, ii) a lens system and iii) means for deflecting the distal end of the hollow tube. The deflection of the hollow tube is in directions transverse to the longitudinal extension of the hollow tube so as to form an optical scan pattern.

The hollow tube is characterized by having mechanical stiffness larger than the optical guide to be received.

As used herein the term spring element is a flexible elastic object, i.e. a hollow tube, which can be displaced sideways by deflecting means. Deflecting means refer herein to, e.g. a scanning motor. Example of scanning motors in alternative embodiments may comprise an electromagnet, a permanent magnet, an electrostatic force, a sonic force, and electromechanical force, a piezoelectric actuator or the like. As used herein the hollow tube has the function of providing circumferential surrounding for the guide and it could be of any shape suitable for the function of confining and being used for displacing the guide e.g. square, triangular or circular.

The invention is particularly, but not exclusively, advantageous for increasing the freedom of optimization of the system described in the prior art. In the prior art the optical guide is supposed to provide light guidance and mechanical stiffness. The advantage of the present invention derives from the splitting of these two functionalities, as the dependence of the mechanical properties belongs to the hollow tube while the dependence of the optical properties depends on the guide. Yet another advantage of the invention is that the system becomes more robust and the assembly simpler.

A further advantage of the invention is that it may facilitate the construction of the means for deflecting the distal end of the hollow tube, e.g. a scanning motor. Building a robust optical guide motor inside the housing with an optical guide as spring element is difficult because the stiffness of the guide is relatively low. In order to have a sufficiently rigid motor construction, the free length of the guide must be relatively short. Generally the combination of low stiffness, short bending length and small diameter requires the motor characteristics to be very sensitive to the mechanical tolerances of the guide. Moreover in case in which another type of guide, with slightly different mechanical properties, is desirable, the characteristics of the motor have to be adapted. This invention, which increases the robustness of the spring element by using a hollow tube, has the advantage of facilitating the construction of the motor by loosening its requirements.

Moreover, the improved robustness of the system improves the possible constructive parameter range and the location of the motor parts. The scanning motor is indeed located inside the housing of the probe allowing for downscaling of the system.

A further advantage of the invention may be the absence of a resonator, e.g. a tuning fork which would allow only resonant scanning. The presence of the hollow tube allows for resonant and non resonant scanning. In case of resonant scanning the hollow tube may have symmetric or asymmetric cross-sectional profile. In specific application of resonant scanning asymmetric cross-sectional profile may be advantageous because of the different resonant frequencies between the major and minor axes of the tube, which may give a favourite scanning direction.

In one embodiment the optical scanning probe assembly may comprises an optical guide with an outer diameter fitting inside an inner diameter of the hollow tube. The insertion into the hollow tube allows adjusting the position of the guide in order to find the optimal focus of the system. The optical guide may have any desired dimension within the inner diameter of the hollow tube. The optical guide may be held inside the hollow tube by securing means. In the present context securing means are for example plastic or rubber jacket on the optical guide, which in connection with a proper selection of inner and outer diameters would result in the guide having a tight fit inside the hollow tube or for example a releasable screw or spring, being fixed in relation to the hollow tube, for engaging the optical guide. A glue, e.g. a UV curable glue, may be further used for secure the guide to the hollow tube once its position has been adjusted.

In the present context the hollow tube is not to be formed or put around the guide, but the guide is to be inserted in the tube. Therefore the hollow tube has to be self-supporting and has to be able to carry the mount and lens system without collapsing. Hence, a plastic jacket or a coating as often seen on optical guides is not a hollow tube according to the invention.

In another embodiment the lens system is connected to the distal end of the hollow tube by a mount and is centered on the longitudinal axis of the hollow tube. The presence of a mount is particularly advantageous as it avoids the direct attachment of the lenses to the guide which generally weakens the robustness of the optical guide. Another advantage of the presence of the mount is that the system can be mechanically tested before the introduction of the guide.

In an advantageous embodiment a proximal end part of the hollow tube is fixed inside the housing. The distance between the fixed part of the hollow tube and the end of the hollow tube is defined as the free length of the hollow tube. The free length of the hollow tube may have different values depending on the material of the guide and the desired resonant properties of the spring element, and can be selected in the construction of the scanning motor.

In a further embodiment the housing forms part of an endoscope, a catheter, a needle, or a biopsy needle.

The mechanical properties of the spring element are preferably characterized by an extensive material property such as its mechanical stiffness (MS). Here, the mechanical stiffness may be defined as the resistance of the spring element, here the hollow tube, to deflection or bending by an applied force. It may be measured by $$MS = \frac{P}{\rho},$$

where P is a steady transverse pressure applied to the hollow tube and $\rho$ is the deflection of the hollow tube under the applied pressure. The mechanical stiffness is determined by the shape and dimensions of the spring element as well as by the elastic properties of the constituent material, quantified by the Young's elastic modulus.

Where the hollow tube has a circular cross section and is formed in an isotropic material, the mechanical stiffness is $MS_{ht} = E_{ht} \circ (d2^3 - d1^3)$, where $E_{ht}$ is the Young's elastic modulus of the material in which the hollow tube is formed, d2 is the outer diameter of the hollow tube, and d1 is the inner diameter of the hollow tube. Similarly, the where the light guide is a solid rod with a circular cross section and is formed in an isotropic material, the mechanical stiffness is $MS_{lg} = E_{lg} \circ d1^3$, where $E_{lg}$ is the Young's elastic modulus of the material in which the light guide is formed and d1 is the outer diameter of the light guide. These relations can be used to select the overall mechanical stiffness of the spring element, with and without the light guide inside the hollow tube.

In a preferred embodiment the mechanical stiffness of the hollow tube is larger than the mechanical stiffness of the optical light guide. It may be preferred that the mechanical stiffness' fulfill the relation $MS_{ht}/MS_{lg} > 1.05$, more preferably $MS_{ht}/MS_{lg} > 1.5$, or even more preferred $MS_{ht}/MS_{lg} > 2$, $MS_{ht}/MS_{lg} > 5$, or $MS_{ht}/MS_{lg} > 10$. By having $MS_{ht}$ larger than $MS_{lg}$, it may be ensured that the overall mechanical stiffness of the spring element is predominantly determined by the hollow tube and is not sensitive to variations in the mechanical stiffness of the light guide. This provides the advantage that different light guides can be used without significantly changing the mechanical properties of the spring element. This provides the further advantage that the scanning motor can be tested prior to inserting the light guide into the hollow tube.

The following non-exhaustive list of materials provides examples of materials in which the hollow tube may be made: steel (E=210 GPa), glassfiber reinforced plastic (E=7-45 GPa), aluminium (E=69 GPa), Glass (E=72 GPa), titanium (E=105-120 GPa), carbonfiber reinforced plastic (E=70-200 GPa), wolfram (E=400-410 GPa), siliciumcarbide (E=450 GPa). In a preferred embodiment the hollow tube is formed in steel. Typical values of Young's elastic modulus of an optical guide depends on the materials used, e.g. glass (E=±72 GPa) and acrylic glass (PMMA) (E=1.8-3.1 GPa).

The selection of shape and dimensions of the hollow tube, and the elastic modulus of the applied material, are preferably used to determine characteristics of the spring element and thereby of the scanning motor employed in the optical probe. A high stiffness may preferably be obtained by selecting a material with high value for the Young's elastic modulus or by increasing the outer diameter of the hollow tube, or by doing both.

In a second aspect, the invention provides an optical imaging system comprising:

an optical scanning probe assembly according to the first aspect of the invention scanning unit operationally connected to the means for deflecting, for controlling the means for deflecting to form the optical scan pattern;

a radiation source (RS) for providing radiation to be guided by an optical guide held in the hollow tube of the optical scanning probe assembly; and an imaging detector (ID) being arranged for imaging using reflected or emitted radiation from a region of interest (ROI).

In a further aspect, the invention provides a method for optical scanning imaging, the method comprising:

inserting an optical guide in a hollow tube of an optical scanning probe assembly according to the first aspect of the invention;

arranging the optical scanning probe assembly in relation to an optical radiation source (RS) to guide radiation from the radiation source through the optical guide;

adjusting the position of the optical fibre in the longitudinal direction of the hollow tube to control the position of the image of the guided radiation formed by the lens system.

In one embodiment the outer housing of the optical scanning probe assembly comprises an optical window at its distal end part, and wherein the distal end of the optical guide is positioned at a distance (S) away from the lens system, S being selected by adjusting the position of the optical guide in the hollow tube so that a focal point is formed outside the outer housing at a distance in the range [5 µm; 1000 µm], more preferred [10 µm; 500 µm] or even more preferred [10 µm; 200 µm] from the optical window. This embodiment is preferred for imaging in normal tissue where it is assumed that the probe is held so that the optical window touches the tissue to be imaged. By adjusting the position of the guide and therefore by varying the distance S different areas of the tissues can be brought into focus. The distance S generally is significantly larger than the core diameter of the optical fibre. The ratio between the distance S and the fibre diameter at an exit position may be 0.5, 1, 5, 10, 20, 30, or higher.

In yet another embodiment the distal end of the optical guide is positioned at a distance (L) away from the distal end of the hollow tube, L being preferably larger than 5 micron, more preferably larger than 10 micron. This embodiment refers to the effect of the insertion of the guide in the hollow tube: by inserting and adjusting the guide manually, the end of the fibre and the end of the tube may not coincide as the guide is inserted when the probe has been already assembled.

BRIEF DESCRIPTION OF THE DRAWINGS

The present invention will now be explained, by way of example only, with reference to the accompanying figures. The figures show one way of implementing the present invention and is not to be construed as being limiting to other possible embodiments falling within the scope of the attached claim set.

DETAILED DESCRIPTION OF EMBODIMENTS

Figure 1:
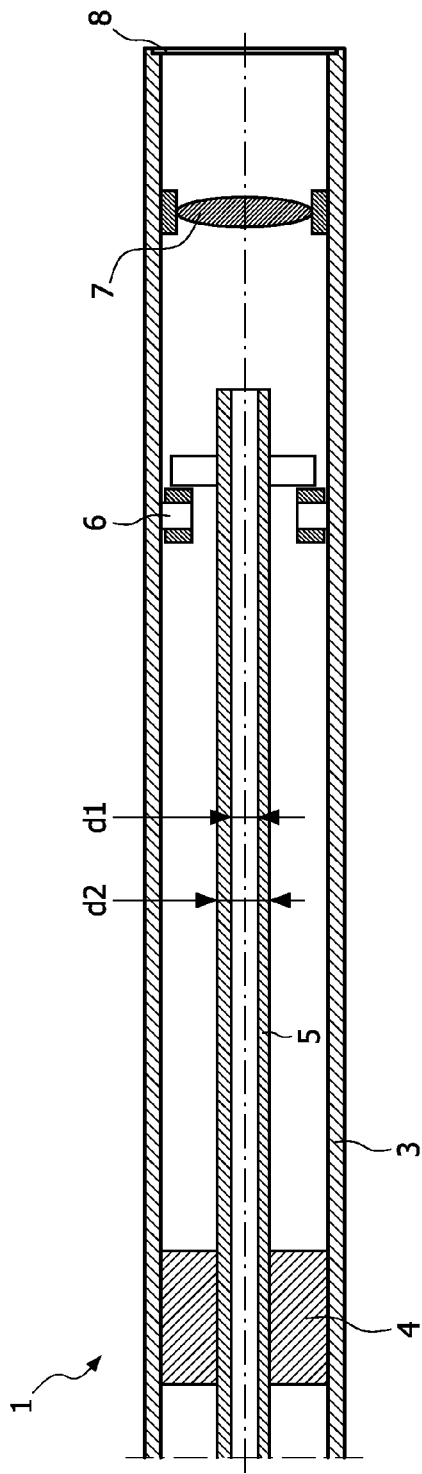
FIG. 1 is a schematic cross-sectional drawing of an optical scanning probe assembly according to the present invention.

FIG. 1 is a schematic cross-sectional drawing of the scanning probe assembly 1 according to the first aspect of the present invention when the optical guide is not inserted. The optical probe 1 comprises an outer housing 3 holding through holding means 4 a hollow tube 5 with an outer diameter d2 of typically 0.8 mm and an inner diameter d1 of typically 0.5 mm. The hollow tube 5 serves as spring element for a scanning motor 6, which in this embodiment is schematically represented as an electromagnet. The lens system 7 is fixed to the housing and the focus of the system is adjusted after the insertion of the optical guide (not shown).

In the context of the present invention it is to be understood that the term "optical guide" may include, and is not limited to, optical fibers (multi-mode and single-mode), thin film optical paths, photonic crystal fibers, photonic bandgap fibers (PBG), polarization maintaining fibers, and the like. The optical probe may also comprise more than one fiber i.e. a plurality of fibers or a fiber bundle.

The housing 3 has at its distal or sampling end a transparent window 8. The window 8 can be a plane section of an optical transport glass or polymer. The window 8 is preferably non-focusing i.e. it has no optical power, but it is contemplated that the window 8 may for some applications have some focusing effect. The probe is normally held so that the window 8 touches the tissue to be imaged. The exit window may also be obliquely mounted with respect to the optical light guide.

For the purpose of illustration, demonstration and instruction, the relation between the mechanical stiffness of the hollow tube, $MS_{ht}$, and the mechanical stiffness of the optical light guide, $MS_{lg}$, is calculated for some exemplary dimensions and materials in the following table. For circular cross sections and isotropic materials, the relation can be written as:

$$\frac{MS_{ht}}{MS_{lg}} = \frac{E_{ht}(d2^3 - d1^3)}{E_{lg}\, d1^3}$$

| d1 [mm] | d2 [mm] | $E_{ht}$ [GPa] | $E_{lg}$ [GPa] | $MS_{ht}/MS_{lg}$ |
|---|---|---|---|---|
| 0.5 | 0.8 | 210 Steel | 72 Glass | 9 |
| 0.5 | 1 | 210 Steel | 72 Glass | 20.4 |
| 0.5 | 0.8 | 35 Reinforced plast | 72 Glass | 1.5 |
| 0.5 | 0.8 | 35 Reinforced plast | 2.5 PMMA | 43.3 |

Figure 2:
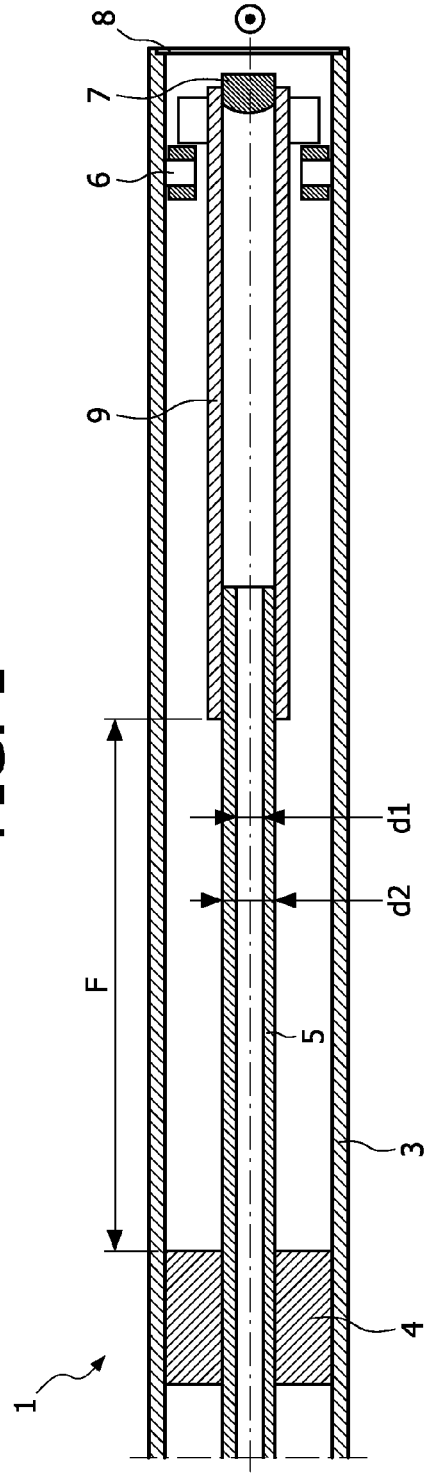
FIG. 2 is a schematic cross-sectional drawing of an embodiment of the optical scanning probe assembly where the lens system is connected to the distal end of the hollow tube through a mount.

FIG. 2 is a schematic cross-sectional drawing of the scanning probe assembly 1 according to one embodiment of the present invention where the lens system 7 is connected to the distal end of the hollow tube 5 by a mount 9 and being centered on the longitudinal axis of the hollow tube. The lens system in this embodiment is fixed to the mount and not to the housing. The free length F of the hollow tube may have different length depending on the material of the guide and on the scanning motor.

Figure 3:
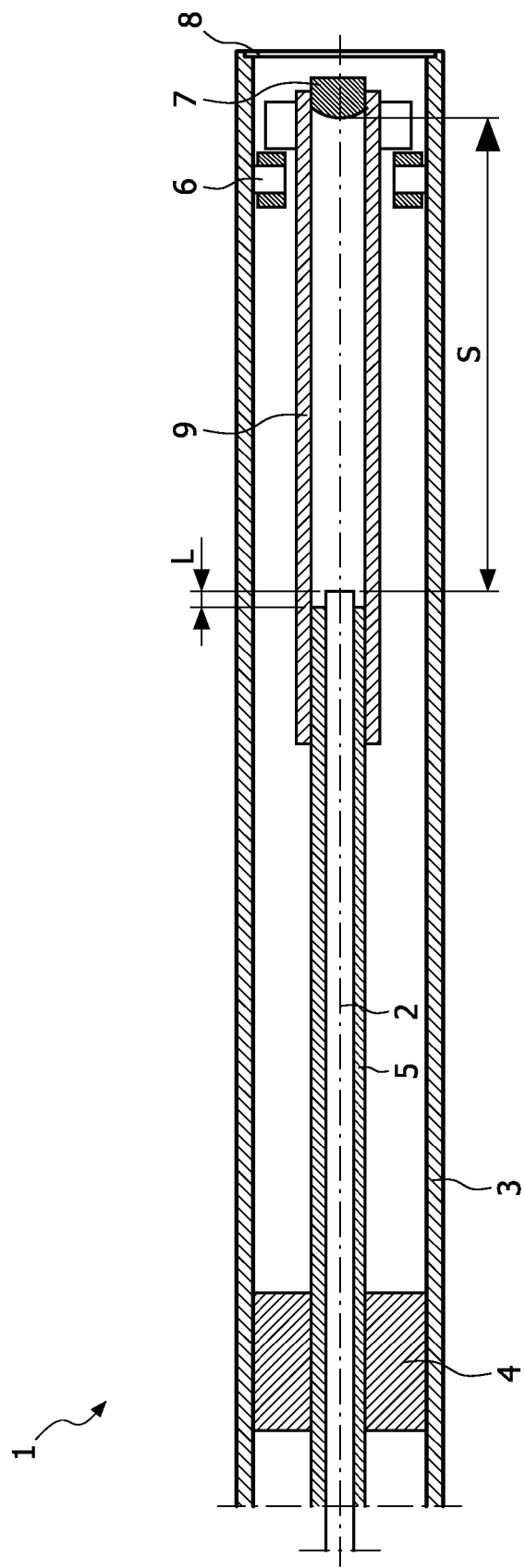
FIG. 3 is a schematic cross-sectional drawing of an embodiment of the optical scanning probe assembly where the lens system is connected to the distal end of the hollow tube through a mount and the optical guide has been inserted.

FIG. 3 is a schematic cross-sectional drawing of the scanning probe assembly 1 according to one embodiment of the present invention when the optical guide 2 is inserted. The end of the guide is typically not at the same position as the end of the tube. The unmatching distal ends are due to the manual insertion of the guide into the probe that has been already assembled before the insertion. The distance L between the end of the guide and the end of the hollow tube 5 is preferably larger than 5 μm or even more preferably larger than 10 μm. In respect to the position of the lens system 7 the distal end of the optical guide is located at a distance S. Variation of the distance S by adjusting the position of the optical guide 9 in the hollow tube 5 allows tuning of the focus of the system.

Figure 4:
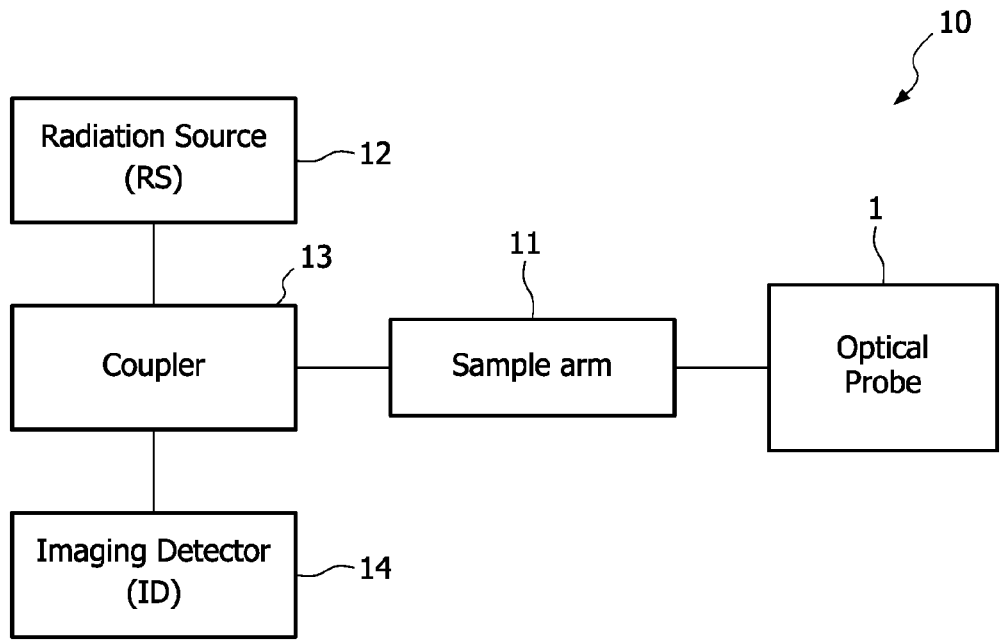
FIG. 4 is a schematic drawing of an optical imaging system according to the present invention.

FIG. 4 is a schematic drawing of an optical imaging system 10 according to the present invention. The optical imaging system comprises an optical probe 1 as described above, the optical probe located at the end of a sample arm 11. The sample arm 11 is preferably highly flexible and bendable to some extent.

Additionally, a radiation source (RS) 12 is optically coupled to the optical probe 1 via a coupler 13. The probe 1 is accordingly arranged for guiding radiation, e.g. laser light, emitted from the radiation source 12 to a region of interest. Furthermore an imaging detector (ID) 14 is optically coupled to the optical probe 1. The imaging detector is arranged for imaging using reflected or emitted radiation from the region of interest in the sample (not shown). The imaging detector 14 may also comprise a user interface (UI) so accessing results and/or controlling the imaging process (not shown).

Figure 5:
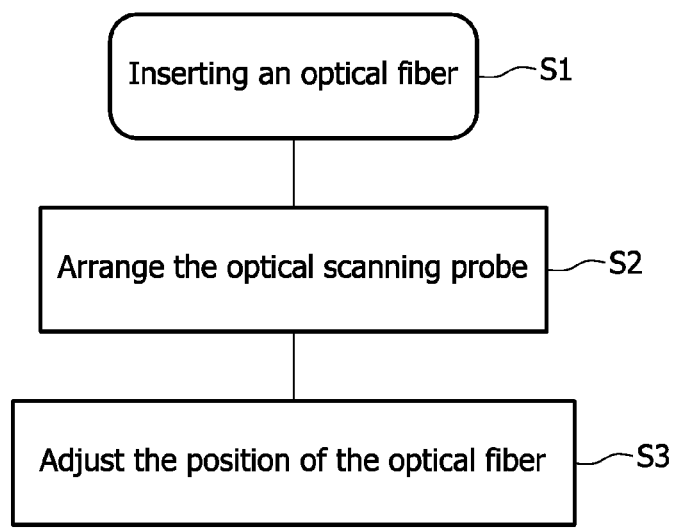
FIG. 5 is a flow-chart of a method for optical scanning imaging according to the invention.

FIG. 5 is a flow chart for a method according to the invention. The method comprises:

S1 inserting an optical guide in a hollow tube of an optical scanning probe assembly according to the first aspect of the invention;

S2 arranging the optical scanning probe assembly in relation to an optical radiation source (RS) to guide radiation from the radiation source through the optical guide;

S3 adjusting the position of the optical fibre in the longitudinal direction of the hollow tube to control the position of the image of the guided radiation formed by the lens system.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An optical scanning probe assembly comprising:
   a housing having a longitudinal axis;
   a hollow tube centered on and extending lengthwise along the longitudinal axis inside the housing;
   a holder for fixedly attaching a portion of the hollow tube to the housing;
   a lens system provided inside the housing;
   a mount having opposite proximal and distal ends, wherein
      at the distal end, the mount is coupled to the lens system, and
      at the proximal end, the mount is coupled to and surrounds a portion of the hollow tube; and
   a scanning motor attached to and inside the housing at a certain distance from the mount for displacing the hollow tube transverse to the longitudinal axis to form an optical scan pattern.

2. The optical scanning probe assembly according to claim 1, further comprising an optical guide for fitting inside the hollow tube.

3. The optical scanning probe assembly according to claim 2, wherein the hollow rube serves as a spring element for the scanning motor, and wherein a mechanical stiffness of the hollow tube is larger than a mechanical stiffness of the optical guide.

4. The optical scanning probe assembly according to claim 3, wherein a result of division of the mechanical stiffness of the hollow tube by the mechanical stiffness of the optical guide is greater than at least one of 1.05 and 1.5.

5. The optical scanning probe assembly according to claim 3, wherein a result of division of the mechanical stiffness of the hollow tube by the mechanical stiffness of the optical guide is greater than at least one of 2 and 5.

6. The optical scanning probe assembly according to claim 3, wherein a result of division of the mechanical stiffness of the hollow tube by the mechanical stiffness of the optical guide is greater than 10.

7. The optical scanning probe assembly of claim 3, wherein the hollow tube has an outer diameter of about 0.8 mm and an inner diameter of about 0.5 mm.

8. The optical scanning probe assembly of claim 2, wherein the optical guide comprises an optical fiber.

9. The optical scanning probe assembly according to c an wherein the lens system is centered on the longitudinal axis.

10. The optical scanning probe assembly according to claim 1, wherein the housing forms a part of any of an endoscope, a catheter, a needle, or a biopsy needle.

11. The optical scanning probe assembly according to claim 2, further comprising an optical window at the distal end, wherein the mount positions the optical guide at a first distance away from the lens system, and the scanning motor is configured to adjust a position of the mount to form a focal point t outside the outer housing at a distance in a range selected from one of 5 µm to 1000 µm, 10 µm to 500 µm, and 10 µm to 200 µm from the optical window.

12. The optical scanning probe assembly according to claim 11, wherein the optical guide is positioned at a second distance extending beyond the hollow tube within the mount, and wherein the second distance is one of larger than 5 micron, and larger than 10 micron.

13. An optical imaging system comprising:
   an optical scanning probe assembly including:
      a housing having a longitudinal axis,
      a hollow tube centered on and extending lengthwise along the longitudinal axis inside the housing,
      a holder for fixedly attaching a portion of the hollow tube to the housing,
      a lens system provided inside the housing,
      a mount having opposite proximal and distal ends, wherein
         at the distal end, the mount is coupled to the lens system, and
         at the proximal end, the mount is coupled to and surrounds a portion of the hollow tube, and
      a scanning motor attached to and inside the housing at a certain distance from the mount for displacing the hollow tube transverse to the longitudinal axis to form an optical scan pattern;
   a scanning unit operationally connected to the scanning motor for controlling the scanning motor to form the optical scan pattern;
   a radiation source for providing radiation guided by an optical guide held in the hollow tube; and
   an imaging detector being arranged for imaging using reflected or emitted radiation from a region of interest.

14. A method for optical scanning imaging, the method comprising the acts of:
   providing an optical scanning probe assembly including:
      a housing having a longitudinal axis;
      a hollow tube centered on and extending lengthwise along the longitudinal axis inside the housing,
      a holder for fixedly attaching a portion of the hollow tube to the housing,
      an optical guide inserted into the hollow tube,
      a lens system provided inside the housing,
      a mount having opposite proximal and distal ends, wherein
         at the distal end, the mount is coupled to the lens system, and
         at the proximal end, the mount is coupled to and surrounds a portion of the hollow tube, and
      a scanning motor attached to and inside the housing at a certain distance from the mount for displacing the hollow tube transverse to the longitudinal axis to form an optical scan pattern;

arranging the optical scanning probe assembly in relation to an optical radiation source to guide radiation from the radiation source through the optical guide; and adjusting a position of the optical guide in a direction along and transverse to the longitudinal axis to control a position of an image of the guided radiation formed by the lens system.

* * * * *